United States Patent
Yildiz et al.

(10) Patent No.: US 11,861,837 B2
(45) Date of Patent: *Jan. 2, 2024

(54) UTILIZATION OF LUMINANCE CHANGES TO DETERMINE USER CHARACTERISTICS

(71) Applicant: Apple Inc., Cupertino, CA (US)

(72) Inventors: Izzet B. Yildiz, Sunnyvale, CA (US); Grant H. Mulliken, San Jose, CA (US); Sterling R. Crispin, Santa Cruz, CA (US)

(73) Assignee: Apple Inc., Cupertino, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/738,606

(22) Filed: May 6, 2022

(65) Prior Publication Data
US 2022/0261999 A1     Aug. 18, 2022

Related U.S. Application Data

(63) Continuation of application No. 16/934,071, filed on Jul. 21, 2020, now Pat. No. 11,354,805.

(60) Provisional application No. 62/880,206, filed on Jul. 30, 2019.

(51) Int. Cl.
    *G06T 7/00*     (2017.01)
    *G06T 11/00*     (2006.01)

(52) U.S. Cl.
    CPC .......... *G06T 7/0014* (2013.01); *G06T 11/001* (2013.01); *G06T 2207/20081* (2013.01); *G06T 2207/30041* (2013.01)

(58) Field of Classification Search
    CPC .................. G06T 7/0014; G06T 11/001; G06T 2207/20081; G06T 2207/30041; G06K 9/00597; G06F 3/013; G06F 3/015
    See application file for complete search history.

(56) References Cited

U.S. PATENT DOCUMENTS

| | | |
|---|---|---|
| 9,596,508 B2 | 3/2017 | McCoy et al. |
| 10,303,245 B2 | 5/2019 | Ha et al. |
| 10,620,700 B2 | 4/2020 | Publicover |
| 2012/0083668 A1 | 4/2012 | Pradeep et al. |
| 2015/0213634 A1 | 7/2015 | Karmarkar et al. |
| 2015/0332166 A1 | 11/2015 | Ferens et al. |
| 2016/0225012 A1 | 8/2016 | Ha et al. |
| 2016/0328015 A1 | 11/2016 | Ha et al. |
| 2017/0131766 A1 | 5/2017 | He et al. |
| 2017/0365101 A1 | 12/2017 | Samec et al. |
| 2018/0255167 A1 | 9/2018 | Saito |

(Continued)

FOREIGN PATENT DOCUMENTS

| | | |
|---|---|---|
| CN | 105453070 A | 3/2016 |
| JP | 2018194931 A | 12/2018 |

(Continued)

OTHER PUBLICATIONS

English Machine Translation of WO 2015/072202 (Year: 2015).*

(Continued)

*Primary Examiner* — Antonio A Caschera
(74) *Attorney, Agent, or Firm* — Thompson Hine LLP (57) ABSTRACT

Identifying a state of a user (e.g., attentive, distracted, mind wandering, etc.) based on the user's physiological (e.g., pupillary) response to luminance change events in which a portion or all of the content quickly becomes brighter or dimmer.

14 Claims, 5 Drawing Sheets

(56) References Cited

U.S. PATENT DOCUMENTS

2018/0365491 A1 12/2018 Delaney
2018/0365875 A1* 12/2018 Yildiz ................. G06V 40/193

FOREIGN PATENT DOCUMENTS

| WO | WO 2015072202 | 5/2015 |
| WO | 2018/100875 A1 | 6/2018 |
| WO | WO20200159784 | 8/2020 |

OTHER PUBLICATIONS

PCT, European Patent Office (ISA/EP), International Search Report and Written Opinion of the International Searching Authority, International Application No. PCT/US2020/042947, 11 pages (dated Oct. 29, 2020).
China National Intellectual Property Administration, Notification to Grant Patent Right for Invention (with partial English translation), Chinese Patent Application No. 202080054433.9, 7 pages, Nov. 1, 2022.

* cited by examiner

UTILIZATION OF LUMINANCE CHANGES TO DETERMINE USER CHARACTERISTICS

CROSS-REFERENCE TO RELATED APPLICATIONS

This application is a continuation of U.S. patent application Ser. No. 16/934,071 filed Jul. 21, 2020, which claims the benefit of U.S. Provisional Application Ser. No. 62/880,206 filed Jul. 30, 2019, each of which is incorporated herein in its entirety.

TECHNICAL FIELD

The present disclosure generally relates to displaying content on electronic devices, and in particular, to systems, methods, and devices for assessing the states of users viewing content displayed on electronic devices.

BACKGROUND

A user's state (e.g., distracted, attentive, etc.) while viewing content on an electronic device can have a significant effect on the user's experience. Content creators and display systems may be able to provide better and more tailored user experiences that a user is more likely to enjoy, comprehend, and learn from based on being able to determine the user's state.

SUMMARY

Attributes of content may result in particular types of physiological responses in users viewing the content. For example, the pupils of users may experience dilation or constriction automatically in response to luminance changes in content, e.g., as the content changes from mostly dim to mostly bright and vice versa. Implementations herein recognize that the physiological response of a user to such a change in content may depend upon the user's state. For example, the magnitude or dynamics of a user's pupillary response to a quick change in luminance may differ depending upon the user's state. For example, if the luminance of the content increases while the user is attentive and engaged, the pupillary response may be slower and smaller in magnitude compared to the situations in which the user is disengaged or fatigued during the same luminance increase. Some implementations disclosed herein identify a state of a user (e.g., attentive, distracted, mind wandering, etc.) based on how the user's physiological (e.g., pupillary) response to luminance change events in which a portion or all of the content quickly becomes brighter or dimmer. Some implementations, improve a user's enjoyment and/or comprehension during a user experience by providing alternative content and/or a suggestion (e.g., that the user take a break) based on detecting the user's state.

In some implementations, a device having a processor, a display, and a sensor implements a method. The method identifies a luminance change event associated with content on the display. The luminance change event may be a relatively quick change to brighter or dimmer content viewed by the user. The luminance change event may occur naturally as the user scans the content or be embedded intentionally in the content for purposes of triggering a response that can be used to assess state. The method uses the sensor to obtain a physiological response (e.g., a pupillary dilation or constriction) of a user perceiving the luminance change event associated with the content on the display. In some implementations, for example, an inward facing camera on a head-mounted device (HMD) captures images of the user's eye and a pupil diameter/radius is determined via a computer vision technique. The method assesses the state of the user based on the pupillary response. The state may be determined based on magnitude and/or dynamics of the pupillary response. In some implementations, the pupillary response is compared with the user's own prior responses to determine the user's current state. In some implementations, the pupillary response is assessed based on pupillary responses of multiple users to various types of content, e.g., comparing the user's current pupillary response with a typical or average user response to a similar luminance change event. In some implementations, the state is determined using statistical or machine learning-based classification techniques.

In accordance with some implementations, a non-transitory computer readable storage medium has stored therein instructions that are computer-executable to perform or cause performance of any of the methods described herein. In accordance with some implementations, a device includes one or more processors, a non-transitory memory, and one or more programs; the one or more programs are stored in the non-transitory memory and configured to be executed by the one or more processors and the one or more programs include instructions for performing or causing performance of any of the methods described herein.

BRIEF DESCRIPTION OF THE DRAWINGS

So that the present disclosure can be understood by those of ordinary skill in the art, a more detailed description may be had by reference to aspects of some illustrative implementations, some of which are shown in the accompanying drawings.

In accordance with common practice the various features illustrated in the drawings may not be drawn to scale. Accordingly, the dimensions of the various features may be arbitrarily expanded or reduced for clarity. In addition, some of the drawings may not depict all of the components of a given system, method or device. Finally, like reference numerals may be used to denote like features throughout the specification and figures.

DESCRIPTION

Numerous details are described in order to provide a thorough understanding of the example implementations shown in the drawings. However, the drawings merely show some example aspects of the present disclosure and are therefore not to be considered limiting. Those of ordinary skill in the art will appreciate that other effective aspects or variants do not include all of the specific details described herein. Moreover, well-known systems, methods, components, devices and circuits have not been described in exhaustive detail so as not to obscure more pertinent aspects of the example implementations described herein.

Figure 1:
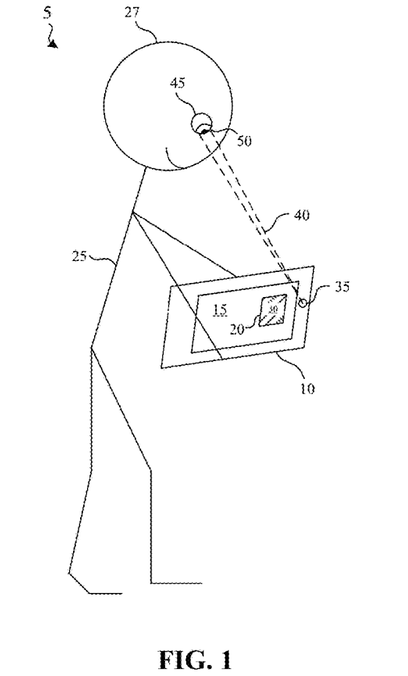
FIG. 1 illustrates a device displaying content and obtaining physiological data from a user according to some implementations.

FIG. 1 illustrates a physical environment 5 including a device 10 with a display 15. The device 10 displays content 20 (including content item 30) to a user 25. The content may include a video, a presentation, other time-varying content, or content presented as part of a computer-generated reality (CGR) environment. The device 10 is configured to obtain physiological data (e.g., pupillary data, electrocardiograph (ECG) data, etc.) from the user 25 via a sensor 35 directed in a direction 40 towards the user 25.

While the device 10 is illustrated as a hand-held device, other implementations involve devices with which a user interacts without holding and devices worn by a user. In some implementations, as illustrated in FIG. 1, the device 10 is a handheld electronic device (e.g., a smartphone or a tablet). In some implementations the device 10 is a laptop computer or a desktop computer. In some implementations, the device 10 has a touchpad and, in some implementations, the device 10 has a touch-sensitive display (also known as a "touch screen" or "touch screen display"). In some implementations, the device 10 is a wearable head mounted display (HMD) for example, worn on a head 27 of the user 25.

Moreover, while this example and other examples discussed herein illustrate a single device 10 in a physical environment 5, the techniques disclosed herein are applicable to multiple devices as well as to multiple real world environments. For example, the functions of device 10 may be performed by multiple devices.

In some implementations, the device 10 includes an eye tracking system for detecting eye position and eye movements. For example, an eye tracking system may include one or more infrared (IR) light-emitting diodes (LEDs), an eye tracking camera (e.g., near-IR (NIR) camera), and an illumination source (e.g., an NIR light source) that emits light (e.g., NIR light) towards the eyes of the user 25. Moreover, the illumination source of the device 10 may emit NIR light to illuminate the eyes of the user 25 and the NIR camera may capture images of the eyes of the user 25. In some implementations, images captured by the eye tracking system may be analyzed to detect position and movements of the eyes of the user 25, or to detect other information about the eyes such as pupil dilation or pupil diameter. Moreover, the point of gaze estimated from the eye tracking images may enable gaze-based interaction with content.

In some implementations, the device 10 has a graphical user interface (GUI), one or more processors, memory and one or more modules, programs or sets of instructions stored in the memory for performing multiple functions. In some implementations, the user 25 interacts with the GUI through finger contacts and gestures on the touch-sensitive surface. In some implementations, the functions include image editing, drawing, presenting, word processing, website creating, disk authoring, spreadsheet making, game playing, telephoning, video conferencing, e-mailing, instant messaging, workout support, digital photographing, digital videoing, web browsing, digital music playing, and/or digital video playing. Executable instructions for performing these functions may be included in a computer readable storage medium or other computer program product configured for execution by one or more processors.

In some implementations, the device 10 employs various physiological sensor, detection, or measurement systems. Detected physiological data may include, but is not limited to, electroencephalography (EEG), electrocardiography (ECG), electromyography (EMG), functional near infrared spectroscopy signal (fNIRS), blood pressure, skin conductance, or pupillary response. Moreover, the device 10 may simultaneously detect multiple forms of physiological data in order to benefit from synchronous acquisition of physiological data. Moreover, in some implementations, the physiological data represents involuntary data, e.g., responses that are not under conscious control. For example, a pupillary response may represent an involuntary movement.

In some implementations, one or both eyes 45 of the user 25, including one or both pupils 50 of the user 25 present physiological data in the form of a pupillary response. The pupillary response of the user 25 results in a varying of the size or diameter of the pupil 50, via the optic and oculomotor cranial nerve. For example, the pupillary response may include a constriction response (miosis), e.g., a narrowing of the pupil, or a dilation response (mydriasis), e.g., a widening of the pupil. In some implementations, the device 10 may detect patterns of physiological data representing a time-varying pupil diameter.

Figure 2:
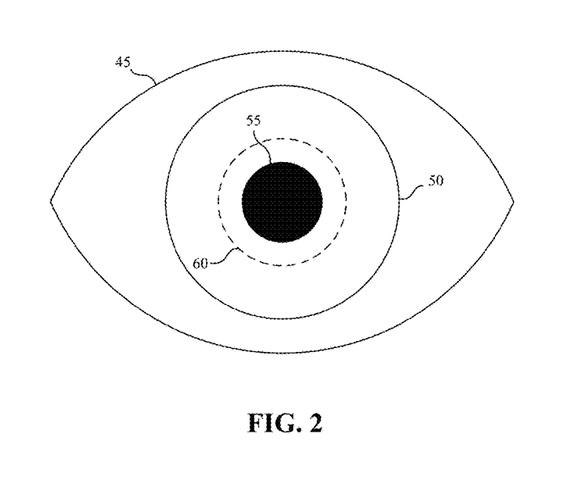
FIG. 2 illustrates a pupil of the user of FIG. 1 in which the diameter of the pupil varies.

FIG. 2 illustrates a pupil 50 of the user 25 of FIG. 1 in which the diameter of the pupil 50 varies with time. As shown in FIG. 2, a present physiological state (e.g., present pupil diameter 55) may vary in contrast to a past physiological state (e.g., past pupil diameter 60). For example, the present physiological state may include a present pupil diameter and a past physiological state may include a past pupil diameter. The physiological data may represent a response pattern that dynamically varies over time.

The device 10 may use the physiological data to implement the techniques disclosed herein. For example, a user's pupillary response to a luminance change event in the content may be compared with the user's prior responses to similar luminance change events in the same or other content.

Figure 3:
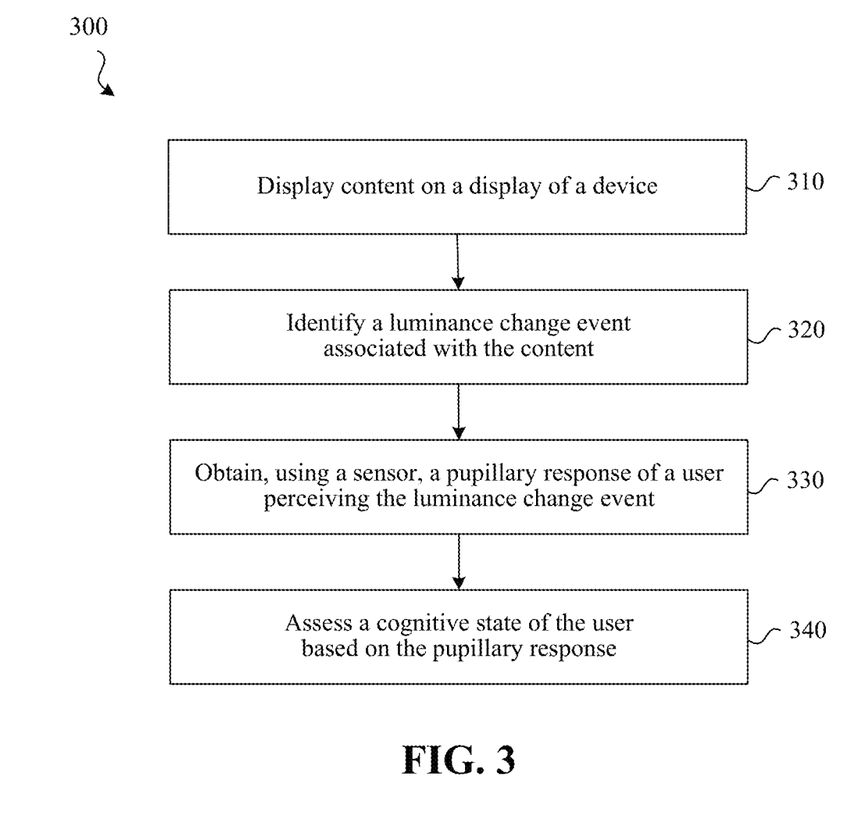
FIG. 3 is a flowchart representation of a method for identifying a state of a user based on how the user's pupil responds to a luminance change event.

FIG. 3, in accordance with some implementations, is a flowchart representation of a method 300 for identifying a state of a user based on how the user's pupil responds to a luminance change event. In some implementations, the method 300 is performed by one or more devices (e.g., device 10). The method 300 can be performed at a mobile device, HMD, desktop, laptop, or server device. The method 300 can be performed on an HMD that has a screen for displaying 3D images or a screen for viewing stereoscopic images. In some implementations, the method 300 is performed by processing logic, including hardware, firmware, software, or a combination thereof. In some implementations, the method 300 is performed by a processor executing code stored in a non-transitory computer-readable medium (e.g., a memory).

At block 310, the method 300 displays content on a display of a device. The content may include a video, a presentation, other time-varying content, or content presented as part of a computer-generated reality (CGR) environment. A computer-generated reality (CGR) environment refers to a wholly or partially simulated environment that people sense and/or interact with via an electronic system. In CGR, a subset of a person's physical motions, or representations thereof, are tracked, and, in response, one or more characteristics of one or more virtual objects simulated in the CGR environment are adjusted in a manner that comports with at least one law of physics. For example, a CGR system may detect a person's head turning and, in response, adjust graphical content and an acoustic field presented to the person in a manner similar to how such views and sounds would change in a physical environment. In some situations (e.g., for accessibility reasons), adjustments to characteristic(s) of virtual object(s) in a CGR environment may be made in response to representations of physical motions (e.g., vocal commands).

A person may sense and/or interact with a CGR object using any one of their senses, including sight, sound, touch, taste, and smell. For example, a person may sense and/or interact with audio objects that create 3D or spatial audio environment that provides the perception of point audio sources in 3D space. In another example, audio objects may enable audio transparency, which selectively incorporates ambient sounds from the physical environment with or without computer-generated audio. In some CGR environments, a person may sense and/or interact only with audio objects.

Examples of CGR include virtual reality and mixed reality. A virtual reality (VR) environment refers to a simulated environment that is designed to be based entirely on computer-generated sensory inputs for one or more senses. A VR environment comprises virtual objects with which a person may sense and/or interact. For example, computer-generated imagery of trees, buildings, and avatars representing people are examples of virtual objects. A person may sense and/or interact with virtual objects in the VR environment through a simulation of the person's presence within the computer-generated environment, and/or through a simulation of a subset of the person's physical movements within the computer-generated environment.

In contrast to a VR environment, which is designed to be based entirely on computer-generated sensory inputs, a mixed reality (MR) environment refers to a simulated environment that is designed to incorporate sensory inputs from the physical environment, or a representation thereof, in addition to including computer-generated sensory inputs (e.g., virtual objects). On a virtuality continuum, a mixed reality environment is anywhere between, but not including, a wholly physical environment at one end and virtual reality environment at the other end.

In some MR environments, computer-generated sensory inputs may respond to changes in sensory inputs from the physical environment. Also, some electronic systems for presenting an MR environment may track location and/or orientation with respect to the physical environment to enable virtual objects to interact with real objects (that is, physical articles from the physical environment or representations thereof). For example, a system may account for movements so that a virtual tree appears stationery with respect to the physical ground.

Examples of mixed realities include augmented reality and augmented virtuality. An augmented reality (AR) environment refers to a simulated environment in which one or more virtual objects are superimposed over a physical environment, or a representation thereof. For example, an electronic system for presenting an AR environment may have a transparent or translucent display through which a person may directly view the physical environment. The system may be configured to present virtual objects on the transparent or translucent display, so that a person, using the system, perceives the virtual objects superimposed over the physical environment. Alternatively, a system may have an opaque display and one or more imaging sensors that capture images or video of the physical environment, which are representations of the physical environment. The system composites the images or video with virtual objects, and presents the composition on the opaque display. A person, using the system, indirectly views the physical environment by way of the images or video of the physical environment, and perceives the virtual objects superimposed over the physical environment. As used herein, a video of the physical environment shown on an opaque display is called "pass-through video," meaning a system uses one or more image sensor(s) to capture images of the physical environment, and uses those images in presenting the AR environment on the opaque display. Further alternatively, a system may have a projection system that projects virtual objects into the physical environment, for example, as a hologram or on a physical surface, so that a person, using the system, perceives the virtual objects superimposed over the physical environment.

An augmented reality environment also refers to a simulated environment in which a representation of a physical environment is transformed by computer-generated sensory information. For example, in providing pass-through video, a system may transform one or more sensor images to impose a select perspective (e.g., viewpoint) different than the perspective captured by the imaging sensors. As another example, a representation of a physical environment may be transformed by graphically modifying (e.g., enlarging) portions thereof, such that the modified portion may be representative but not photorealistic versions of the originally captured images. As a further example, a representation of a physical environment may be transformed by graphically eliminating or obfuscating portions thereof.

An augmented virtuality (AV) environment refers to a simulated environment in which a virtual or computer generated environment incorporates one or more sensory inputs from the physical environment. The sensory inputs may be representations of one or more characteristics of the physical environment. For example, an AV park may have virtual trees and virtual buildings, but people with faces photorealistically reproduced from images taken of physical people. As another example, a virtual object may adopt a shape or color of a physical article imaged by one or more imaging sensors. As a further example, a virtual object may adopt shadows consistent with the position of the sun in the physical environment.

There are many different types of electronic systems that enable a person to sense and/or interact with various CGR environments. Examples include head mounted systems, projection-based systems, heads-up displays (HUDs), vehicle windshields having integrated display capability, windows having integrated display capability, displays formed as lenses designed to be placed on a person's eyes (e.g., similar to contact lenses), headphones/earphones, speaker arrays, input systems (e.g., wearable or handheld controllers with or without haptic feedback), smartphones, tablets, and desktop/laptop computers. A head mounted system may have one or more speaker(s) and an integrated opaque display. Alternatively, a head mounted system may be configured to accept an external opaque display (e.g., a smartphone). The head mounted system may incorporate one or more imaging sensors to capture images or video of the physical environment, and/or one or more microphones to capture audio of the physical environment. Rather than an opaque display, a head mounted system may have a transparent or translucent display. The transparent or translucent display may have a medium through which light representative of images is directed to a person's eyes. The display may utilize digital light projection, OLEDs, LEDs, uLEDs, liquid crystal on silicon, laser scanning light source, or any combination of these technologies. The medium may be an optical waveguide, a hologram medium, an optical combiner, an optical reflector, or any combination thereof. In one embodiment, the transparent or translucent display may be configured to become opaque selectively. Projection-based systems may employ retinal projection technology that projects graphical images onto a person's retina. Projection systems also may be configured to project virtual objects into the physical environment, for example, as a hologram or on a physical surface.

At block 320, the method 300 identifies a luminance change event associated with the content. The luminance change may be a quick change to brighter or dimmer content that is detected by monitoring and tracking the luminance of the content over time. The luminance change may be a change in brightness (e.g., average brightness) exceeding a threshold value within a predetermined time period.

In some implementations, pixel information is collected and the collected RGB values (or other pixel values) are converted into an estimated perceived luminance. The luminance may be determined using a linear formula (e.g., LUM=(0.21 Red(R)+0.72 Green(G)+0.07 Blue(B)) or non-linear formula (e.g., LUM=sqrt($0.299R^2+0.587G^2+0.115B^2$)).

The luminance change event may occur naturally as the user scans the content, for example, as the user looks from a brightly lit object to a dimly lit object within the content.

The luminance change event may be embedded intentionally in the content. In one example, artificial luminance probes (e.g., small abrupt luminance changes) are inserted into the content once every few seconds. In another example, artificial luminance probes are sequential (e.g., inserted with a specific frequency over a few seconds).

In some implementations, the luminance change is foveal, e.g., involving changing luminance of a single or group of items upon which the user is focusing. The items upon which the user is focusing may be determined via eye tracking and scene segmentation algorithms. In some implementations, a gaze point is determined and objects within a circular region around the gaze point are considered for the luminance change event detection. The radius or other dimensions of the region of focus may be personalized based on the particular user's gaze characteristics.

In some implementations, the luminance change event is extra-foveal, e.g., involving luminance change occurring outside of a region (e.g., a circular region) around the current focus.

In some implementations, the luminance change event is feature-based, e.g., luminance changes based on the changing in intensity of certain colored objects or specific textures in a scene.

In some implementations, the luminance change is achieved by altering inter-frame content. For example, head-mounted devices (HMDs) may use low persistent displays that briefly display black between rendered frames (either through hardware or software means). These inter-frame moments may be intentionally altered to result in luminance change events within the content over time. For example, some inter-frame may be altered to display white, grey, or otherwise brighter content than would otherwise be displayed.

At block 330, the method 300 obtains, using a sensor, a pupillary response of a user perceiving the luminance change event. In some implementations, the diameter of the pupil is measured over a period of time using an eye-tracking system. In some implementations, images captured by the eye tracking system may be analyzed to detect positions and movements of the eyes of the user and to detect other information about the eyes, such as pupil dilation or pupil diameter. In some implementations, an eye tracking system implemented in a head-mounted device (HMD) collects pupil radius data as a user engages with content.

At block 340, the method 300 assesses a state of the user based on the pupillary response. Examples of user states include, but are not limited to, attentive, inattentive, perceptive, focused, imperceptive, distracted, interested, disinterested, curious, inquisitive, doubtful, critical, certain, deciding, assessing, assessing logically, assessing emotionally, receptive, unreceptive, day-dreaming, thinking, observing, relaxed, processing information, relating to past experience, remembering, mindful, mind-wandering, tired, rested, alert, attracted, repelled, guilty, and indignant. Assessing the state of the user may involve determining a level or extent of a type of state, e.g., determining the extent of attentiveness or an extent of inattentiveness on a numerical scale. As a particular example, depending on the pupillary response magnitude the method 300 may determine that a user was attentive with a score of 0.6 on a normalized scale from 0 to 1 (0 being inattentive and 1 being fully focused).

In some implementations, the method 300 may classify or otherwise determine more than two states depending on the dynamics of the pupillary response after a luminance event (for example, based on how long it takes for pupil radius to reach a minimum, how quickly the pupil radius returns to a normal level, or other dynamic behavior of the pupil). For example, the method 300 may be configured to determine that the user is inattentive and further configured to determine that a reason that the user is inattentive is because the user is tired, rested but day-dreaming, distracted etc. The method may use machine learning models for such sub-category classifications.

In some implementations, the state is determined based on a magnitude of change of pupil diameter or radius. In some implementations, the state is determined based on a pattern or other dynamics of the pupillary response.

In some implementations, the state is determined using a statistical or machine learning-based classification technique. In some implementations, pupil responses are aggregated and classified into different states using statistical or machine-learning based techniques. For example, a machine-learning models may be trained to classify a pupillary response to a luminance change event into one or a fixed number of classes. In one example, a pupillary response is classified as attentive, inattentive, or neutral. In another example, a pupillary response is classified as observing or processing information.

In some implementations, the pupillary response is compared with the user's own prior responses to determine the user's current state. In some implementations, the pupillary response is assessed based on pupillary response of multiple users to various types of content, e.g., comparing the user's current pupillary response with a typical or average user response to a similar luminance change event.

Observing repeated responses of the pupil to luminance changes over a duration of time (e.g., seconds to minutes) may provide insights about the underlying state of the user at different time scales. These luminance changes may occur naturally with the content, occur as the user scans different locations of the screen of the device, or can be embedded into the content, unnoticeable to the user, for example, using minor adaptations to the underlying RGB (or gray) scale of the pixel values.

In some implementations, the method 300 provides feedback to the user based on the user's state. For example, the method 300 may detect an attention lapse and provide a notification for the user to take a break, re-watch a particular portion of the content, or change the content presentation speed. In another example, the method 300 may detect a heightened attention moment in the content and suggest similar moments of content for the user. In another example, a notification may be provided for a user to view content at a particular time or under particular conditions based on determining a state profile for the user. For example, such a profile may indicate that the user is more attentive in the mornings than in the afternoon or evening and a notification may be provided at 8:30 am suggesting to the user that now is a good time to study or work with the content.

In some implementations, the method 300 provides feedback to a content creator to facilitate improvements to the content or future/related content. A notification may identify a portion of the content associated with a state for one or more users, e.g., identifying that during a particular portion of the content users were typically less attentive than during another portion of the content. In some implementations, state data for multiple users who have viewed the content is aggregated to provide feedback regarding the content. The content creator may revise the content based on such feedback to make that portion shorter or more attention grabbing.

In some implementations, content is automatically adjusted or presented according to automatically-determined display parameters based on a user's state. For example, content may be broken up into smaller pieces with breaks in between based on determining that the user is in a particular state.

The method 300 provides a flexible and subtle way to determine the attention levels and other states of a user without requiring a behavioral response and interruption. The method 300 may be provided to users who want to learn a new skill, watch a lecture, or perform a task that requires a long attention span, amongst numerous other uses cases, and may provide such users with information to facilitate the users' purposes. For example, the method 300 may inform a user when his or her attention is low and suggest a break. Such feedback may allow more productive working and learning schedules.

Figure 4:
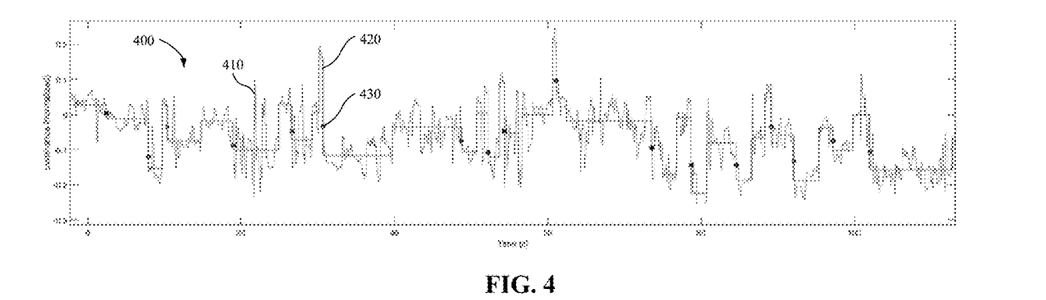
FIG. 4 is a chart illustrating exemplary foveal luminance recordings.

FIG. 4 is a chart 400 illustrating exemplary foveal luminance recordings 410 from a user watching an instructional cooking video. The mean luminance value 420 fluctuates over time as the user's eyes saccade and the content changes. Time instances when the luminance rapidly decreases are indicated with dots (e.g., dot 430). In some implementations, physiological (e.g., pupillary) responses may be measured for a few seconds after each instance in which the luminance rapidly decreases. Similarly, physiological (e.g., pupillary) responses may be measured for a few seconds after each instance in which the luminance rapidly increases.

Figure 5:
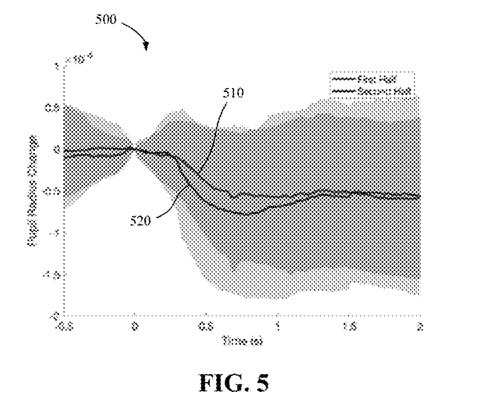
FIG. 5 is a chart illustrating pupil radius responses to luminance increases.

FIG. 5 is a chart 500 illustrating average pupil radius responses to the luminance increases in FIG. 4. In this example, the average pupil radius responses to sudden luminance increases during the first half 510 are different than the average pupil radius responses to sudden luminance increases during the second half 520. For example, the average magnitude of change of the pupil radius was greater during the second half than the first half. In some implementations, larger pupil responses are associated with a relatively inattentive state. Thus, the differences in the average pupil radius responses may indicate that the user was in a more attentive state while viewing the first half of the content than while viewing the second half of the content. Note that shaded areas in the chart represent standard deviation.

Figure 6:
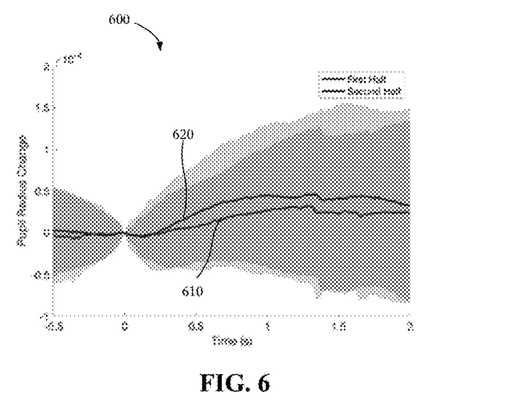
FIG. 6 is a chart illustrating pupil radius responses to luminance decreases.

FIG. 6 is a chart 600 illustrating average pupil radius responses to the luminance decreases in FIG. 4. In this example, the average pupil radius responses to sudden luminance decreases during the first half 610 are different than the average pupil radius responses to sudden luminance decreases during the second half 620. For example, the average magnitude of change of the pupil radius was greater during the second half than the first half. In some implementations, larger pupil responses are associated with a relatively inattentive state. Thus, the differences in the average pupil radius responses may indicate that the user was in a more attentive state while viewing the first half of the content than while viewing the second half of the content. Note that shaded areas in the chart represent standard deviation.

Figure 7:
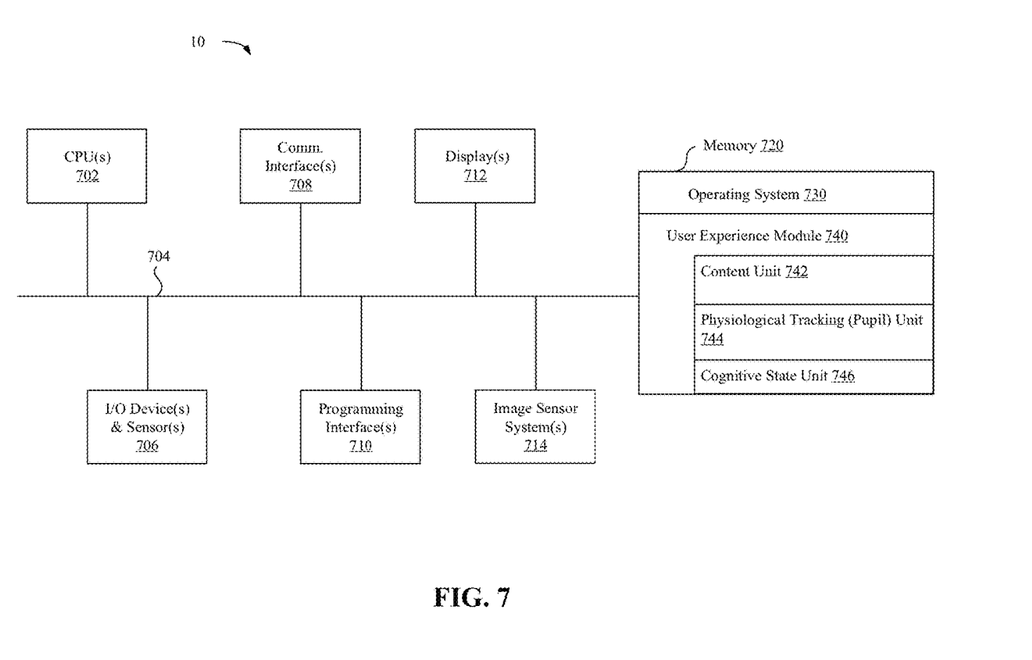
FIG. 7 is a block diagram illustrating device components of an exemplary device according to some implementations.

FIG. 7 is a block diagram of an example of a device 10 in accordance with some implementations. While certain specific features are illustrated, those skilled in the art will appreciate from the present disclosure that various other features have not been illustrated for the sake of brevity, and so as not to obscure more pertinent aspects of the implementations disclosed herein. To that end, as a non-limiting example, in some implementations the device 10 includes one or more processing units 702 (e.g., microprocessors, ASICs, FPGAs, GPUs, CPUs, processing cores, and/or the like), one or more input/output (I/O) devices and sensors 706, one or more communication interfaces 708 (e.g., USB, FIREWIRE, THUNDERBOLT, IEEE 802.3x, IEEE 802.11x, IEEE 802.16x, GSM, CDMA, TDMA, GPS, IR, BLUETOOTH, ZIGBEE, SPI, I2C, and/or the like type interface), one or more programming (e.g., I/O) interfaces 710, one or more displays 712, one or more interior and/or exterior facing image sensor systems 714, a memory 720, and one or more communication buses 704 for interconnecting these and various other components.

In some implementations, the one or more communication buses 704 include circuitry that interconnects and controls communications between system components. In some implementations, the one or more I/O devices and sensors 706 include at least one of an inertial measurement unit (IMU), an accelerometer, a magnetometer, a gyroscope, a thermometer, one or more physiological sensors (e.g., blood pressure monitor, heart rate monitor, blood oxygen sensor, blood glucose sensor, etc.), one or more microphones, one or more speakers, a haptics engine, one or more depth sensors (e.g., a structured light, a time-of-flight, or the like), and/or the like.

In some implementations, the one or more displays 712 are configured to present a user experience to the user 25. In some implementations, the one or more displays 712 correspond to holographic, digital light processing (DLP), liquid-crystal display (LCD), liquid-crystal on silicon (LCoS), organic light-emitting field-effect transitory (OLET), organic light-emitting diode (OLED), surface-conduction electron-emitter display (SED), field-emission display (FED), quantum-dot light-emitting diode (QD-LED), microelectromechanical system (MEMS), a retinal projection system, and/or the like display types. In some implementations, the one or more displays 712 correspond to diffractive, reflective, polarized, holographic, etc. waveguide displays. In one example, the device 10 includes a single display. In another example, the device 10 includes a display for each eye of the user 25, e.g., an HMD. In some implementations, the one or more displays 712 are capable of presenting CGR content.

In some implementations, the one or more image sensor systems 714 are configured to obtain image data that corresponds to at least a portion of the face of the user 25 that includes the eyes of the user 25. For example, the one or more image sensor systems 714 include one or more RGB camera (e.g., with a complimentary metal-oxide-semiconductor (CMOS) image sensor or a charge-coupled device (CCD) image sensor), monochrome camera, IR camera, event-based camera, and/or the like. In various implementations, the one or more image sensor systems 714 further include illumination sources that emit light upon the portion of the face of the user 25, such as a flash or a glint source.

The memory 720 includes high-speed random-access memory, such as DRAM, SRAM, DDR RAM, or other random-access solid-state memory devices. In some implementations, the memory 720 includes non-volatile memory, such as one or more magnetic disk storage devices, optical disk storage devices, flash memory devices, or other non-volatile solid-state storage devices. The memory 720 optionally includes one or more storage devices remotely located from the one or more processing units 702. The memory 720 comprises a non-transitory computer readable storage medium. In some implementations, the memory 720 or the non-transitory computer readable storage medium of the memory 720 stores the following programs, modules and data structures, or a subset thereof including an optional operating system 730 and a user experience module 740.

The operating system 730 includes procedures for handling various basic system services and for performing hardware dependent tasks. In some implementations, the user experience module 740 is configured to display content on electronic devices assess the states of users viewing such content. To that end, in various implementations, the user experience module 740 includes a content unit 742, a physiological tracking (e.g., pupil) unit 744, and a user state unit 746.

In some implementations, the content unit 742 is configured to provide and/or track content for display on a device. The content unit 742 may be configured to monitor and track the luminance of the content over time and/or to identify luminance change events that occur within the content. In some implementations, the content unit 742 may be configured to inject artificial luminance change events into content using one or more of the techniques discussed herein or as otherwise may be appropriate. To these ends, in various implementations, the unit includes instructions and/or logic therefor, and heuristics and metadata therefor.

In some implementations, the physiological tracking (e.g., pupil) unit 744 is configured to track a user's pupil or other physiological attributes using one or more of the techniques discussed herein or as otherwise may be appropriate. To these ends, in various implementations, the unit includes instructions and/or logic therefor, and heuristics and metadata therefor.

In some implementations, the user state unit 746 is configured to assess the state of a user based on a physiological response using one or more of the techniques discussed herein or as otherwise may be appropriate. To these ends, in various implementations, the unit includes instructions and/or logic therefor, and heuristics and metadata therefor.

Although the units and modules of FIG. 7 are shown as residing on a single device (e.g., the device 10), it should be understood that in other implementations, any combination of these units may be located in separate computing devices.

Moreover, FIG. 7 is intended more as functional description of the various features which are present in a particular implementation as opposed to a structural schematic of the implementations described herein. As recognized by those of ordinary skill in the art, items shown separately could be combined and some items could be separated. For example, some functional modules shown separately in FIG. 7 could be implemented in a single module and the various functions of single functional blocks could be implemented by one or more functional blocks in various implementations. The actual number of modules and the division of particular functions and how features are allocated among them will vary from one implementation to another and, in some implementations, depends in part on the particular combination of hardware, software, and/or firmware chosen for a particular implementation.

Figure 8:
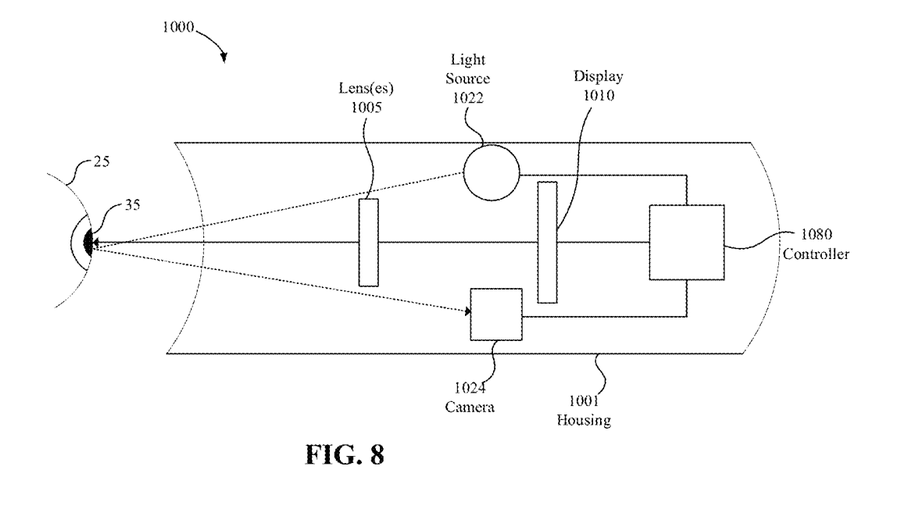
FIG. 8 is a block diagram of an example head-mounted device (HMD) in accordance with some implementations.

FIG. 8 illustrates a block diagram of an exemplary head-mounted device 1000 in accordance with some implementations. The head-mounted device 1000 includes a housing 1001 (or enclosure) that houses various components of the head-mounted device 1000. The housing 1001 includes (or is coupled to) an eye pad (not shown) disposed at a proximal (to the user 25) end of the housing 1001. In various implementations, the eye pad is a plastic or rubber piece that comfortably and snugly keeps the head-mounted device 1000 in the proper position on the face of the user 25 (e.g., surrounding the eye of the user 25).

The housing 1001 houses a display 1010 that displays an image, emitting light towards or onto the eye of a user 25. In various implementations, the display 1010 emits the light through an eyepiece having one or more lenses 1005 that refracts the light emitted by the display 1010, making the display appear to the user 25 to be at a virtual distance farther than the actual distance from the eye to the display 1010. For the user 25 to be able to focus on the display 1010, in various implementations, the virtual distance is at least greater than a minimum focal distance of the eye (e.g., 7 cm). Further, in order to provide a better user experience, in various implementations, the virtual distance is greater than 1 meter.

The housing 1001 also houses a tracking system including one or more light sources 1022, camera 1024, and a controller 1080. The one or more light sources 1022 emit light onto the eye of the user 25 that reflects as a light pattern (e.g., a circle of glints) that can be detected by the camera 1024. Based on the light pattern, the controller 1080 can determine an eye tracking characteristic of the user 25. For example, the controller 1080 can determine a gaze direction and/or a blinking state (eyes open or eyes closed) of the user 25. As another example, the controller 1080 can determine a pupil center, a pupil size, or a point of regard. Thus, in various implementations, the light is emitted by the one or more light sources 1022, reflects off the eye of the user 25, and is detected by the camera 1024. In various implementations, the light from the eye of the user 25 is reflected off a hot mirror or passed through an eyepiece before reaching the camera 1024.

The display 1010 emits light in a first wavelength range and the one or more light sources 1022 emit light in a second wavelength range. Similarly, the camera 1024 detects light in the second wavelength range. In various implementations, the first wavelength range is a visible wavelength range (e.g., a wavelength range within the visible spectrum of approximately 400-700 nm) and the second wavelength range is a near-infrared wavelength range (e.g., a wavelength range within the near-infrared spectrum of approximately 700-1400 nm).

In various implementations, eye tracking (or, in particular, a determined gaze direction) is used to enable user interaction (e.g., the user 25 selects an option on the display 1010 by looking at it), provide foveated rendering (e.g., present a higher resolution in an area of the display 1010 the user 25 is looking at and a lower resolution elsewhere on the display 1010), or correct distortions (e.g., for images to be provided on the display 1010).

In various implementations, the one or more light sources 1022 emit light towards the eye of the user 25 which reflects in the form of a plurality of glints.

In various implementations, the camera 1024 is a frame/shutter-based camera that, at a particular point in time or multiple points in time at a frame rate, generates an image of the eye of the user 25. Each image includes a matrix of pixel values corresponding to pixels of the image which correspond to locations of a matrix of light sensors of the camera. In implementations, each image is used to measure or track pupil dilation by measuring a change of the pixel intensities associated with one or both of a user's pupils.

In various implementations, the camera 1024 is an event camera comprising a plurality of light sensors (e.g., a matrix of light sensors) at a plurality of respective locations that, in response to a particular light sensor detecting a change in intensity of light, generates an event message indicating a particular location of the particular light sensor.

It will be appreciated that the implementations described above are cited by way of example, and that the present invention is not limited to what has been particularly shown and described hereinabove. Rather, the scope includes both combinations and sub combinations of the various features described hereinabove, as well as variations and modifications thereof which would occur to persons skilled in the art upon reading the foregoing description and which are not disclosed in the prior art.

As described above, one aspect of the present technology is the gathering and use of physiological data to improve a user's experience of an electronic device with respect to using electronic content. The present disclosure contemplates that in some instances, this gathered data may include personal information data that uniquely identifies a specific person or can be used to identify interests, traits, or tendencies of a specific person. Such personal information data can include physiological data, demographic data, location-based data, telephone numbers, email addresses, home addresses, device characteristics of personal devices, or any other personal information.

The present disclosure recognizes that the use of such personal information data, in the present technology, can be used to the benefit of users. For example, the personal information data can be used to improve the content viewing experience. Accordingly, use of such personal information data may enable calculated control of the electronic device. Further, other uses for personal information data that benefit the user are also contemplated by the present disclosure.

The present disclosure further contemplates that the entities responsible for the collection, analysis, disclosure, transfer, storage, or other use of such personal information and/or physiological data will comply with well-established privacy policies and/or privacy practices. In particular, such entities should implement and consistently use privacy policies and practices that are generally recognized as meeting or exceeding industry or governmental requirements for maintaining personal information data private and secure.

For example, personal information from users should be collected for legitimate and reasonable uses of the entity and not shared or sold outside of those legitimate uses. Further, such collection should occur only after receiving the informed consent of the users. Additionally, such entities would take any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices.

Despite the foregoing, the present disclosure also contemplates implementations in which users selectively block the use of, or access to, personal information data. That is, the present disclosure contemplates that hardware or software elements can be provided to prevent or block access to such personal information data. For example, in the case of user-tailored content delivery services, the present technology can be configured to allow users to select to "opt in" or "opt out" of participation in the collection of personal information data during registration for services. In another example, users can select not to provide personal information data for targeted content delivery services. In yet another example, users can select to not provide personal information, but permit the transfer of anonymous information for the purpose of improving the functioning of the device.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data. For example, content can be selected and delivered to users by inferring preferences or settings based on non-personal information data or a bare minimum amount of personal information, such as the content being requested by the device associated with a user, other non-personal information available to the content delivery services, or publicly available information.

In some embodiments, data is stored using a public/private key system that only allows the owner of the data to decrypt the stored data. In some other implementations, the data may be stored anonymously (e.g., without identifying and/or personal information about the user, such as a legal name, username, time and location data, or the like). In this way, other users, hackers, or third parties cannot determine the identity of the user associated with the stored data. In some implementations, a user may access their stored data from a user device that is different than the one used to upload the stored data. In these instances, the user may be required to provide login credentials to access their stored data.

Numerous specific details are set forth herein to provide a thorough understanding of the claimed subject matter. However, those skilled in the art will understand that the claimed subject matter may be practiced without these specific details. In other instances, methods, apparatuses, or systems that would be known by one of ordinary skill have not been described in detail so as not to obscure claimed subject matter.

Unless specifically stated otherwise, it is appreciated that throughout this specification discussions utilizing the terms such as "processing," "computing," "calculating," "determining," and "identifying" or the like refer to actions or processes of a computing device, such as one or more computers or a similar electronic computing device or devices, that manipulate or transform data represented as physical electronic or magnetic quantities within memories, registers, or other information storage devices, transmission devices, or display devices of the computing platform.

The system or systems discussed herein are not limited to any particular hardware architecture or configuration. A computing device can include any suitable arrangement of components that provides a result conditioned on one or more inputs. Suitable computing devices include multipurpose microprocessor-based computer systems accessing stored software that programs or configures the computing system from a general purpose computing apparatus to a specialized computing apparatus implementing one or more implementations of the present subject matter. Any suitable programming, scripting, or other type of language or combinations of languages may be used to implement the teachings contained herein in software to be used in programming or configuring a computing device.

Implementations of the methods disclosed herein may be performed in the operation of such computing devices. The order of the blocks presented in the examples above can be varied for example, blocks can be re-ordered, combined, or broken into sub-blocks. Certain blocks or processes can be performed in parallel.

The use of "adapted to" or "configured to" herein is meant as open and inclusive language that does not foreclose devices adapted to or configured to perform additional tasks or steps. Additionally, the use of "based on" is meant to be open and inclusive, in that a process, step, calculation, or other action "based on" one or more recited conditions or values may, in practice, be based on additional conditions or value beyond those recited. Headings, lists, and numbering included herein are for ease of explanation only and are not meant to be limiting.

It will also be understood that, although the terms "first," "second," etc. may be used herein to describe various objects, these objects should not be limited by these terms. These terms are only used to distinguish one object from another. For example, a first node could be termed a second node, and, similarly, a second node could be termed a first node, which changing the meaning of the description, so long as all occurrences of the "first node" are renamed consistently and all occurrences of the "second node" are renamed consistently. The first node and the second node are both nodes, but they are not the same node.

The terminology used herein is for the purpose of describing particular implementations only and is not intended to be limiting of the claims. As used in the description of the implementations and the appended claims, the singular forms "a," "an," and "the" are intended to include the plural forms as well, unless the context clearly indicates otherwise. It will also be understood that the term "or" as used herein refers to and encompasses any and all possible combinations of one or more of the associated listed items. It will be further understood that the terms "comprises" or "comprising," when used in this specification, specify the presence of stated features, integers, steps, operations, objects, or components, but do not preclude the presence or addition of one or more other features, integers, steps, operations, objects, components, or groups thereof.

As used herein, the term "if" may be construed to mean "when" or "upon" or "in response to determining" or "in accordance with a determination" or "in response to detecting," that a stated condition precedent is true, depending on the context. Similarly, the phrase "if it is determined [that a stated condition precedent is true]" or "if [a stated condition precedent is true]" or "when [a stated condition precedent is true]" may be construed to mean "upon determining" or "in response to determining" or "in accordance with a determination" or "upon detecting" or "in response to detecting" that the stated condition precedent is true, depending on the context.

The foregoing description and summary of the invention are to be understood as being in every respect illustrative and exemplary, but not restrictive, and the scope of the invention disclosed herein is not to be determined only from the detailed description of illustrative implementations but according to the full breadth permitted by patent laws. It is to be understood that the implementations shown and described herein are only illustrative of the principles of the present invention and that various modification may be implemented by those skilled in the art without departing from the scope and spirit of the invention.

What is claimed is:

1. A method of assessing state of a user, the method comprising:
   at a device comprising a processor, a display, and a sensor:
      identifying a luminance change event associated with content on the display;
      obtaining, using the sensor, a pupillary response of a user perceiving the luminance change event associated with the content on the display;
      determining a magnitude of the pupillary response of the user to the luminance change event;
      assessing a state of the user based on the magnitude of pupillary response of the user perceiving the luminance change, wherein a first state is determined where the magnitude of the pupillary response is relatively larger than a magnitude associated with a prior pupillary response while a second state is determined where the magnitude of the pupillary response is relatively smaller than the magnitude associated with the prior pupillary response; and
      providing a response based on the state of the user, wherein the response comprises:
         a suggestion for the user to rewatch a particular portion of the content;
         a suggestion for the user to change a presentation speed of the content;
         a suggestion identifying a similar moment in other content; or
         a suggestion for the user to view the content or other content at a particular time or under particular conditions.

2. The method of claim 1, wherein the response comprises a suggestion, feedback, or notification to the user.

3. The method of claim 1, wherein the response comprises a suggestion for the user to take a break.

4. A method of assessing state of a user,
   the method comprising:
   at a device comprising a processor, a display, and a sensor:
      identifying a luminance change event associated with content on the display;
      obtaining, using the sensor, a pupillary response of a user perceiving the luminance change event associated with the content on the display;
      determining a magnitude of the pupillary response of the user to the luminance change event;
      assessing a state of the user based on the magnitude of pupillary response of the user perceiving the luminance change, wherein a first state is determined where the magnitude of the pupillary response is relatively larger than a magnitude associated with a prior pupillary response while a second state is determined where the magnitude of the pupillary response is relatively smaller than the magnitude associated with the prior pupillary response; and providing a response based on the state of the user, wherein the response comprises providing alternative content for the user to view instead of the content.

5. A method of assessing state of a user, the method comprising:

at a device comprising a processor, a display, and a sensor:
identifying a luminance change event associated with content on the display;
obtaining, using the sensor, a pupillary response of a user perceiving the luminance change event associated with the content on the display;
determining a magnitude of the pupillary response of the user to the luminance change event;
assessing a state of the user based on the magnitude of pupillary response of the user perceiving the luminance change, wherein a first state is determined where the magnitude of the pupillary response is relatively larger than a magnitude associated with a prior pupillary response while a second state is determined where the magnitude of the pupillary response is relatively smaller than the magnitude associated with the prior pupillary response; and
providing a response based on the state of the user, wherein the response comprises automatically adjusting the content or content display parameters.

6. A method of assessing state of a user, the method comprising:

at a device comprising a processor, a display, and a sensor:
identifying a luminance change event associated with content on the display;
obtaining, using the sensor, a pupillary response of a user perceiving the luminance change event associated with the content on the display;
determining a magnitude of the pupillary response of the user to the luminance change event;
assessing a state of the user based on the magnitude of pupillary response of the user perceiving the luminance change, wherein a first state is determined where the magnitude of the pupillary response is relatively larger than a magnitude associated with a prior pupillary response while a second state is determined where the magnitude of the pupillary response is relatively smaller than the magnitude associated with the prior pupillary response; and
providing a response based on the state of the user, wherein the response comprises breaking the content into multiple pieces with breaks between.

7. A method of assessing state of a user, the method comprising:

at a device comprising a processor, a display, and a sensor:
identifying a luminance change event associated with content on the display;
obtaining, using the sensor, a pupillary response of a user perceiving the luminance change event associated with the content on the display;
determining a magnitude of the pupillary response of the user to the luminance change event;
assessing a state of the user based on the magnitude of pupillary response of the user perceiving the luminance change, wherein a first state is determined where the magnitude of the pupillary response is relatively larger than a magnitude associated with a prior pupillary response while a second state is determined where the magnitude of the pupillary response is relatively smaller than the magnitude associated with the prior pupillary response; and
providing a response based on the state of the user, wherein the response comprises providing feedback to a creator of the content.

8. The method of claim 7, wherein the the feedback identifies a portion of the content associated with one or more users exhibiting the state.

9. A system comprising:

a non-transitory computer-readable storage medium; and
one or more processors coupled to the non-transitory computer-readable storage medium, wherein the non-transitory computer-readable storage medium comprises program instructions that, when executed on the one or more processors, cause the system to perform operations comprising:
identifying a luminance change event associated with content on a display;
obtaining, using a sensor, a pupillary response of a user perceiving the luminance change event associated with the content on the display;
determining a magnitude of the pupillary response of the user to the luminance change event;
assessing a state of the user based on the magnitude of pupillary response of the user perceiving the luminance change, wherein a first state is determined where the magnitude of the pupillary response is relatively larger than a magnitude associated with a prior pupillary response while a second state is determined where the magnitude of the pupillary response is relatively smaller than the magnitude associated with the prior pupillary response; and
providing a response based on the state of the user, wherein the response comprises:
a suggestion for the user to rewatch a particular portion of the content;
a suggestion for the user to change a presentation speed of the content;
a suggestion identifying a similar moment in other content; or
a suggestion for the user to view the content or other content at a particular time or under particular conditions.

10. The system of claim 9, wherein the response comprises a suggestion, feedback, or notification to the user.

11. The system of claim 9, wherein the response comprises providing alternative content for the user to view instead of the content.

12. The system of claim 9, wherein the response comprises automatically adjusting the content or content display parameters.

13. The system of claim 9, wherein the response comprises breaking the content into multiple pieces with breaks between.

14. A non-transitory computer-readable storage medium storing program instructions executable via one or more processors to perform operations comprising:

identifying a luminance change event associated with content on a display;
obtaining, using a sensor, a pupillary response of a user perceiving the luminance change event associated with the content on the display;

determining a magnitude of the pupillary response of the user to the luminance change event;

assessing a state of the user based on the magnitude of pupillary response of the user perceiving the luminance change, wherein a first state is determined where the magnitude of the pupillary response is relatively larger than a magnitude associated with a prior pupillary response while a second state is determined where the magnitude of the pupillary response is relatively smaller than the magnitude associated with the prior pupillary response; and providing a response based on the state of the user, wherein the response comprises:

a suggestion for the user to rewatch a particular portion of the content;

a suggestion for the user to change a presentation speed of the content;

a suggestion identifying a similar moment in other content; or a suggestion for the user to view the content or other content at a particular time or under particular conditions.

\* \* \* \* \*